United States Patent
Sughrue et al.

(10) Patent No.: US 11,238,589 B2
(45) Date of Patent: Feb. 1, 2022

(54) MEDICAL IMAGING WITH INVALID DATA REMOVAL

(71) Applicant: Omniscient Neurotechnology Pty Limited, Sydney (AU)

(72) Inventors: Michael Edward Sughrue, Sydney (AU); Stephane Philippe Doyen, Glebe (AU); Peter James Nicholas, South Hurstville (AU)

(73) Assignee: Omniscient Neurotechnology Pty Limited, Sydney (AU)

( * ) Notice: Subject to any disclaimer, the term of this patent is extended or adjusted under 35 U.S.C. 154(b) by 0 days.

(21) Appl. No.: 16/919,836

(22) Filed: Jul. 2, 2020

(65) Prior Publication Data

US 2022/0005196 A1 Jan. 6, 2022

(51) Int. Cl.
*A61B 5/11* (2006.01)
*G06T 7/00* (2017.01)
(Continued)

(52) U.S. Cl.
CPC ............ *G06T 7/0014* (2013.01); *A61B 5/11* (2013.01); *G16H 30/20* (2018.01); *G16H 30/40* (2018.01);
(Continued)

(58) Field of Classification Search
CPC .......... A61B 5/055; A61B 6/12; A61B 6/507; A61B 3/113; A61B 5/0816; A61B 5/113;
(Continued)

(56) References Cited

U.S. PATENT DOCUMENTS 5,303,051 A * 4/1994 Levesque ......... G08B 13/19602
348/229.1
8,600,135 B2 * 12/2013 Patriarche ............ G06K 9/3233
382/131

(Continued)

OTHER PUBLICATIONS

Li et al., Image Corruption Detection in Diffusion Tensor Imaging for Post-Processing and Real-Time Monitoring, Oct. 25, 2013 [retrieved Jan. 15, 2021], PLOS ONE, vol. 8, Issue 10, 11 pages. Retrieved: https://journals.plos.org/plosone/article?id=10.1371/journal.pone.0049764 (Year: 2013).*

(Continued)

*Primary Examiner* — Matthew C Bella
*Assistant Examiner* — Dennis Rosario
(74) *Attorney, Agent, or Firm* — Fish & Richardson P.C.

(57) ABSTRACT

The following provides an exemplary method. An image is generated. Scan data generated by the sensing of a subject brain is received and a sequence of volumetric-images are accessed. For at least some of the voxels in at least some of the volumetric images, a change value is determined for the voxel by comparing the current-intensity value of the voxel to the adjacent-intensity value of the comparison voxel. For at least some of the plurality volumetric images, a first-aggregate is determined using at least a mean value of change values of the volumetric image and a second-aggregate is determined using at least a median value of change values of the volumetric image. At least one, but not all, of the volumetric images is determined as invalid as a result of the aggregates.

18 Claims, 6 Drawing Sheets

(51) Int. Cl.
*G16H 30/40* (2018.01)
*G16H 30/20* (2018.01)

(52) U.S. Cl.
CPC ............... *G06T 2207/10016* (2013.01); *G06T 2207/10088* (2013.01); *G06T 2207/30016* (2013.01)

(58) Field of Classification Search
CPC ....... A61B 5/02416; A61B 5/11; A61B 5/112; G06T 7/0012; G06T 2207/30016; G06T 2207/10088; G06T 2207/30004; G06T 2207/10132; G06T 2207/30096; G06T 7/20; G06T 11/003; G06T 11/005; G06T 2207/10072; G06T 2207/10081; G06T 2207/10124; G06T 2207/20182; G06T 2207/30104; G06T 5/002; G06T 2207/10104; G06T 2207/20201; G06T 2210/41; G06T 7/215; G06T 2207/10064; G06T 2207/10016; G06T 7/0016; H04N 19/176; H04N 19/52; H04N 19/105
See application file for complete search history.

(56) References Cited

U.S. PATENT DOCUMENTS

| | | | | |
|---|---|---|---|---|
| 10,222,441 | B2* | 3/2019 | Kaditz | G01R 33/48 |
| 10,387,765 | B2* | 8/2019 | Mailhe | G06N 3/084 |
| 10,846,892 | B2* | 11/2020 | Iwase | G06T 7/337 |
| 2008/0281184 | A1* | 11/2008 | White | G01R 33/4806 600/410 |
| 2009/0231453 | A1* | 9/2009 | Huang | H04N 5/23222 348/220.1 |
| 2011/0044524 | A1* | 2/2011 | Wang | G01R 33/54 382/131 |
| 2015/0062590 | A1 | 3/2015 | Bagherinia | |
| 2018/0260981 | A1* | 9/2018 | Gholipour-Baboli | A61B 5/055 |
| 2020/0205726 | A1* | 7/2020 | Lee | A61B 5/4809 |

OTHER PUBLICATIONS

Becker et al., "Going Beyond Diffusion Tensor Imaging Tractography in Eloquent Glioma Surgery-High-Resolution Fiber Tractography: Q-Ball or Constrained Spherical Deconvolution?" World Neurosurg., Feb. 2020 134:e596-609.

Bonney et al., A Simplified Method of Accurate Postprocessing of Diffusion Tensor Imaging for Use in Brain Tumor Resection, Oper Neurosurg (Hagerstown) 13, 47-59 (2017).

Burks et al., "A method for safely resecting anterior butterfly gliomas: the surgical anatomy of the default mode network and the relevance of its preservation". J. Neurosurg., Sep. 2016, 126(6):1795-811.

Dell'Acqua and Tournier, "Modelling white matter with spherical deconvolution: How and why?" NMR Biomed., 2019, 32:e3945.

Fan et al., "The Human Brainnetome Atlas: A New Brain Atlas Based on Connectional Architecture," Cereb Cortex, 2016, 26:3508-26.

Fischl, "FreeSurfer," Neuroimage, 2012, 62:774-81.

Garyfallidis et al., "Dipy, a library for the analysis of diffusion MRI data," Frontiers in Neuroinformatics, 2014, 8:1-17.

Glasser et al., "A multi-modal parcellation of human cerebral cortex," Nature, 2016, 536:171-8.

Glenn et al., "Common Disconnections in Glioma Surgery: An Anatomic Description," Cureus, 2017, 9:e1778.

Ille et al., Functional Reorganization of Cortical Language Function in Glioma Patients—A Preliminary Study. Frontiers in Oncology 9 (2019).

Jin et al., "Functional and anatomical connectivity-based parcellation of human cingulate cortex." Brain Behav., 2018, 8:e01070.

Ohue et al., "Evaluation of intraoperative brain shift using an ultrasound-linked navigation system for brain tumor surgery," Neurol. Med. Chir., 2010, 50:291-300.

Panesar et al., "Tractography for Surgical Neuro-Oncology Planning: Towards a Gold Standard," Neurotherapeutics, 2019, 16:36-51.

Power et al., "Spurious but systematic correlations in functional connectivity MRI networks arise from subject motion," Neuroimage, Feb. 2012, 59(3):2142-54.

Rijnen et al., "Cognitive functioning in patients with low-grade glioma: effects of hemispheric tumor location and surgical procedure" 2019, 1(4):81-99.

Smitha et al., "Resting state fMRI: A review on methods in resting state connectivity analysis and resting state networks," Neuroradiol. J., 2017, 30:305-17.

Smyser et al., "Longitudinal Analysis of Neural Network Development in Preterm Infants" Cereb Cortex, Dec. 2010, 20(12):2852-62.

Gautam et al., "A Method for Motion Detection and Categorization in Perfusion Weighted MRI," Proceedings of the Eighth Indian Conference on Computer Vision, Graphics and Image Processing, Dec. 2012, Article No. 6, pp. 1-8.

International Search Report and Written Opinion in International Appln. No. PCT/AU2021/050672, dated Aug. 25, 2021, 10 pages.

Marami et al., "Motion-Robust Diffusion Compartment Imaging using Simultaneous Multi-Slice Acquisition," Magnetic Resonance in Medicine, May 2019, 81(5):3314-3329.

* cited by examiner

MEDICAL IMAGING WITH INVALID DATA REMOVAL

TECHNICAL FIELD

This document describes medical imaging technology.

BACKGROUND

Medical imaging includes the technique and process of creating visual representations of the interior of a body for clinical analysis and medical intervention, as well as visual representation of the function of some organs or tissues (physiology). Medical imaging seeks to reveal internal structures hidden by the skin and bones, as well as to diagnose and treat disease. Medical imaging also establishes a database of normal anatomy and physiology to make it possible to identify abnormalities.

SUMMARY

Technology described in this document can be used for generating an image. In one implementation, a method includes receiving scan data generated by the sensing of a subject brain. The method includes accessing a sequence of volumetric-images based on the scan data, each volumetric image i) having an associated time and ii) comprising a plurality of voxels, each voxel having a particular address in the volumetric image. The method includes, for at least some of the voxels in at least some of the volumetric images: accessing a current-intensity value for the voxel; accessing an adjacent-intensity value for a comparison voxel with the particular address in an adjacent volumetric-image in the sequence of volumetric images; and determining a change value for the voxel by comparing the current-intensity value of the voxel to the adjacent-intensity value of the comparison voxel. The method includes, for at least some of the plurality volumetric images, determining a first-aggregate using at least a mean value of change values of the volumetric image; determining a second-aggregate using at least a median value of change values of the volumetric image; comparing the first-aggregate to a first threshold; and comparing the second-aggregate to a second threshold. The method includes marking at least one, but not all, of the volumetric images as invalid as a result of the comparison of the first-aggregate to the first threshold and the comparison of the second-aggregate to the second threshold. The method includes saving in computer memory an image free of the volumetric images marked as invalid. Other implementations can include devices, software, computer-readable media, and products.

Implementations can include all, some, or none of the following features. The method includes accessing the saved image as a motion-corrected image that corrects for an invalid data (e.g., an invalid volumetric image) i) created by operation of a magnetic resonance imager; and ii) that do not correctly represent a phenomenon of the subject brain. Determining a first-aggregate comprises: determining a mean value of all change values of the volumetric image; increasing the mean value with a first function that grows at a first rate greater than linearly; and determining a second-aggregate comprises: determining a median value of all change values of the volumetric image; and increasing the mean value with a second function that grows at a second rate greater than linearly. The first rate is equivalent to the second rate. The method includes validating the scan data based on a determination that no more than a discard-threshold number of volumetric-images are marked as invalid. The method includes validating the first threshold and validating the second threshold based in part on: displaying the image free of the volumetric-images marked as invalid; and receiving, in response to the displaying, user input indicating that the image free of the volumetric-images marked as invalid is usable for a clinical application. The method includes, for at least some of the voxels in at least some of the volumetric images, accessing the particular address of the voxel.

Implementations can provide all, some, or none of the following advantages. The technology of medical imaging is advanced. Volumetric imaging data taken when a patient moves may be utilized using this technology, where otherwise it would be discarded for containing too much invalid data, e.g., too many invalid volumetric images. This can allow for a reduction in the likelihood of "repeat" imaging sessions for patients that move during imaging, which may be of particular value to patients being treated for conditions that cause involuntary movements or patients that require or would benefit from expedited treatment.

DESCRIPTION OF DRAWINGS

Like reference symbols in the various drawings indicate like elements.

DETAILED DESCRIPTION

Described here is technology for generating images without invalid data that can be generated by volumetric imaging devices. For example, a patient receiving a functional magnetic resonance imaging (fMRI) test may move while some of the data is being generated. This may result in a portion of the imaging being out of alignment with the rest of the imaging and therefore containing invalid imaging data. This document describes technology that can identify portions of volumetric data that contain movement-caused invalid data and can exclude this data from a volumetric image created from the volumetric data. Invalid data can be understood as imaging data that is not useful as part of creating an accurate medical image for a diagnostic or research purpose or to assist with treatment.

Figure 1:
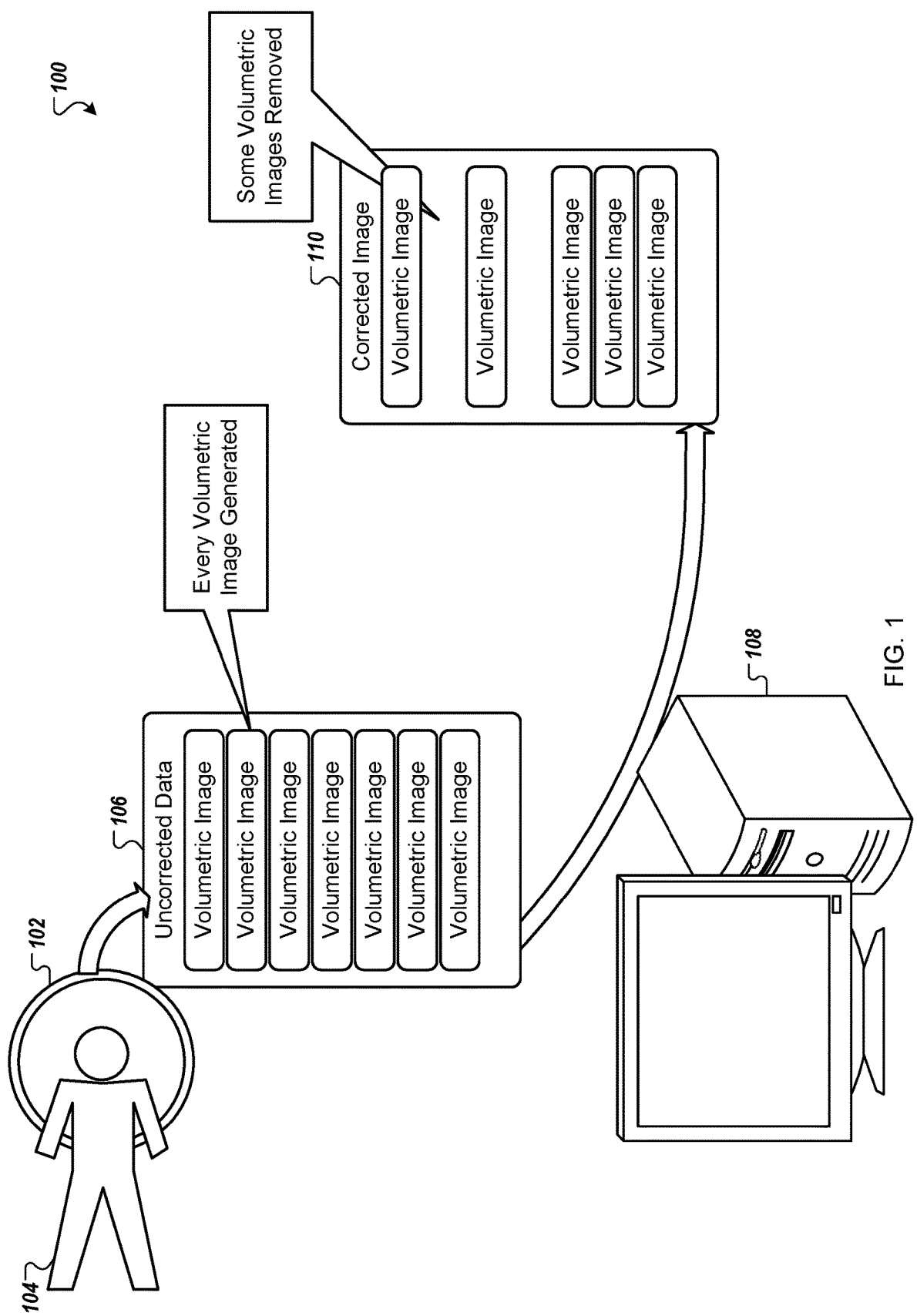
FIG. 1 shows an example system for generating medical images with removal of invalid data.

FIG. 1 shows an example system 100 for generating medical images with invalid data removal. In the system 100, a medical imager 102 images a patient 104 to generate uncorrected data 106 for a clinical-data client 108. The client 108 prepares, from the data 106, a corrected image 110 with no invalid data or less invalid data (e.g., fewer invalid images) than are contained in the uncorrected data 106. The resulting corrected image series 110 may then be used for an array of clinical uses such as diagnostic analysis, surgery planning, automated analysis, etc.

When the medical imager 102 generates uncorrected data 106, sometimes a patient 104 will shift or move while a scan is being performed. This can result in a corresponding layer in the uncorrected data 106 recording the patient in a different orientation than the rest of the layers. As such, this layer contains invalid data that does not represent the physiology of the patient 104 in the same ways that the rest of the data 106 does.

When subjecting the uncorrected data 106 to analysis, such invalid data may produce anomalous results ranging from a reduction in accuracy and/or completely incorrect results. As such, the client 108 may apply one or more invalid data removal techniques to the uncorrected data 106 in order to produce a corrected image series 110. For example, by examining layers of the data 106, the client 108 can identify one or more layers as producing invalid data e.g., as a result of movement by the patient. These layers in the data 106 can be excluded when creating the image 110. As such, the creation of the image 110 represents an improvement in the technology of volumetric sensing in that superior-accuracy images 110 can be produced compared to lower-accuracy data 106.

The medical imager 102 represents any sort of device that generates medical images, including DICOM or similar images. Examples include MM machines, computed tomography machines, X-Ray machines, and ultrasound machines, which can be used in fields including, but not limited to, radiology, cardiology, oncology, nuclear medicine, radiotherapy, neurology, orthopedics, obstetrics, gynecology, ophthalmology, dentistry, maxillofacial surgery, dermatology, pathology, clinical trials, veterinary medicine, and medical/clinical photography.

The clinical-data client 108 represents a general purpose or specific computing device that provides a user with interface elements to manipulate data, including the uploading of imaging data to a cloud-service provider 112. This can include laptop or desktop computers, workstations, servers, telephone devices, tablet devices, control-panels attached to or incorporated with the medical imager 102, etc.

Figure 2:
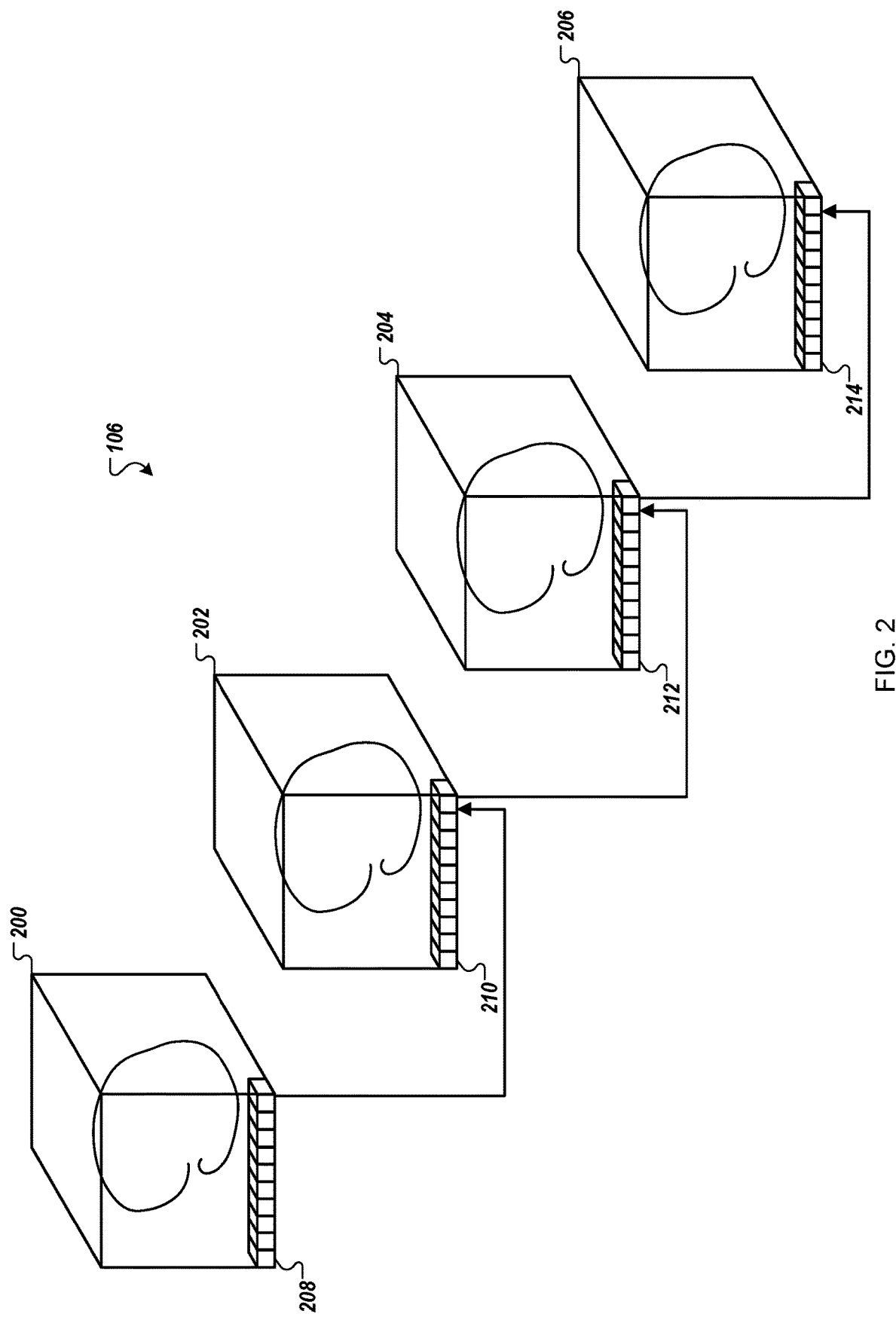
FIG. 2 shows an example of data generated by medical imaging.

FIG. 2 shows an example of data 106 generated by medical imaging. The data 106 may be generated, stored in computer memory, transmitted across computer networks, etc. in binary format. The data 106 can include a plurality of volumetric images 200-206 (more or fewer are possible) that each represent a scan of a brain at a particular timestamp or within a particular timeframe. The particular format of the scan, and the phenomena being recoreded, can vary depending on the type of scan being performed. For example, the data 106 may record the results of a functional magnetic resonance imaging (fMRI) or diffusion tractography.

Each volumetric image 200-206 can incorporate a three-dimensional array of voxels. For clarity, only a single row of voxels 208-214 are shown, but it will be understood that the entirety of the volumetric images 200-206 may be composed of voxels. Each voxel can store one or more values to represent the phenomena being scanned at the corresponding space within or around the patient being scanned. These values may be rendered onto a screen to make a visual representation of the data 106, or may be used in calculations, for example, to aid clinicians in making diagnoses or for other clinical purposes.

The voxels 208-214 can each be uniquely addressed within their volumetric images using the same scheme. For example, each voxel may have an address [X,Y,Z] that identifies the voxel's location in the X, Y, and Z direction from an origin point (e.g., a corner of the volumetric image). By using the same scheme for each volumetric image 200-206, voxels in the same locations in their respective volumetric image may have the same address. As shown here, the voxels in the lower right corner of each volumetric image 200-206 may have the same address (e.g., [9,0,0])

Figure 3:
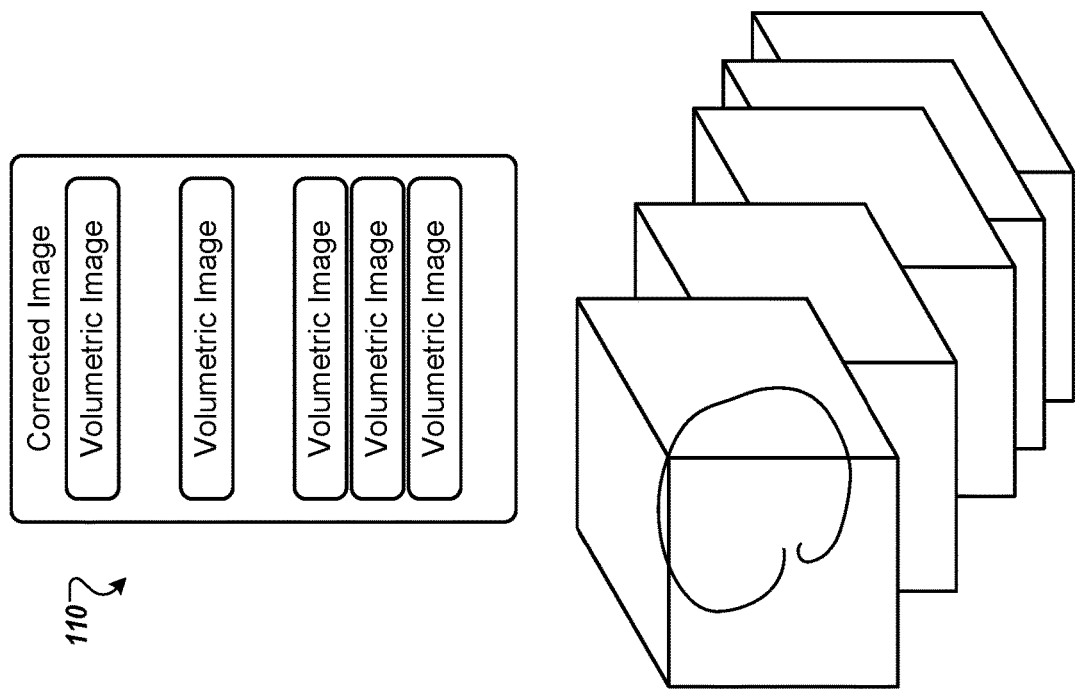
FIG. 3 shows an example of data having invalid data removed.
Figure 3:
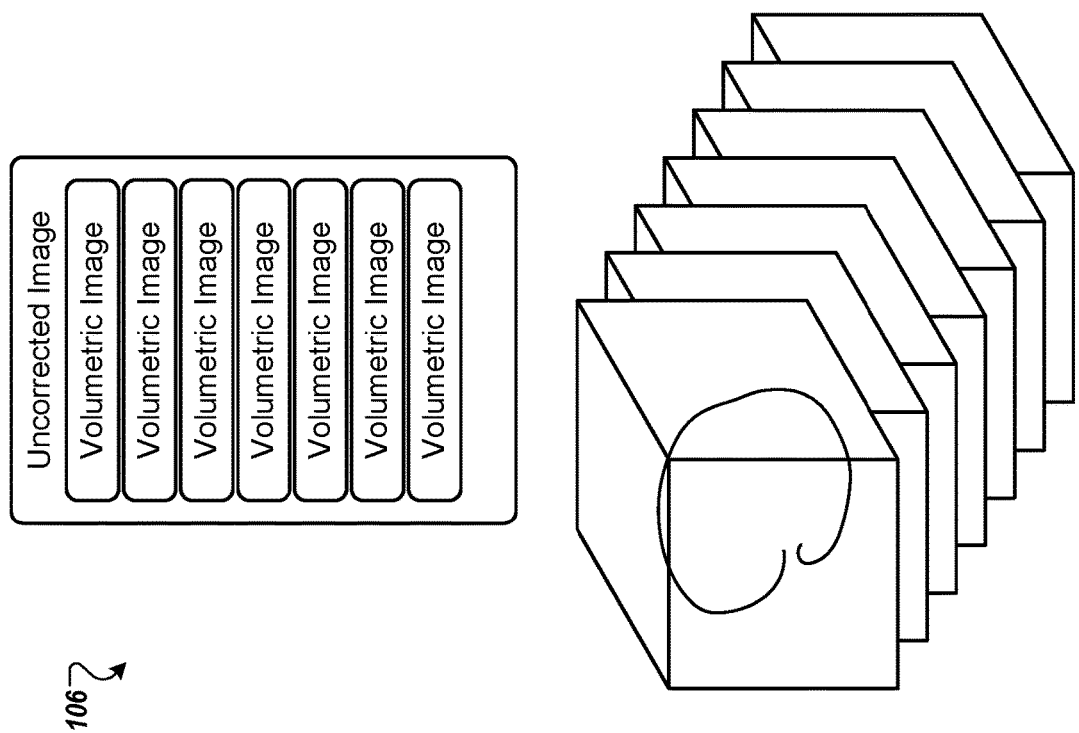

FIG. 3 shows an example of data 106 and an associated image 110 with without invalid data found in the data 106. In the data 106, each volumetric image generated by the scanner 102 is shown. After the data 106 is processed to remove invalid data, the image 110 is created from the volumetric images that are not determined to have the invalid data. As such, the image 110 may have some, but possibly not all, of the volumetric images of the data 106. In some cases, the patient 104 may not move enough to generate invalid data 106, in which case the image 110 may have all of the volumetric images of the data 106.

Figure 4:
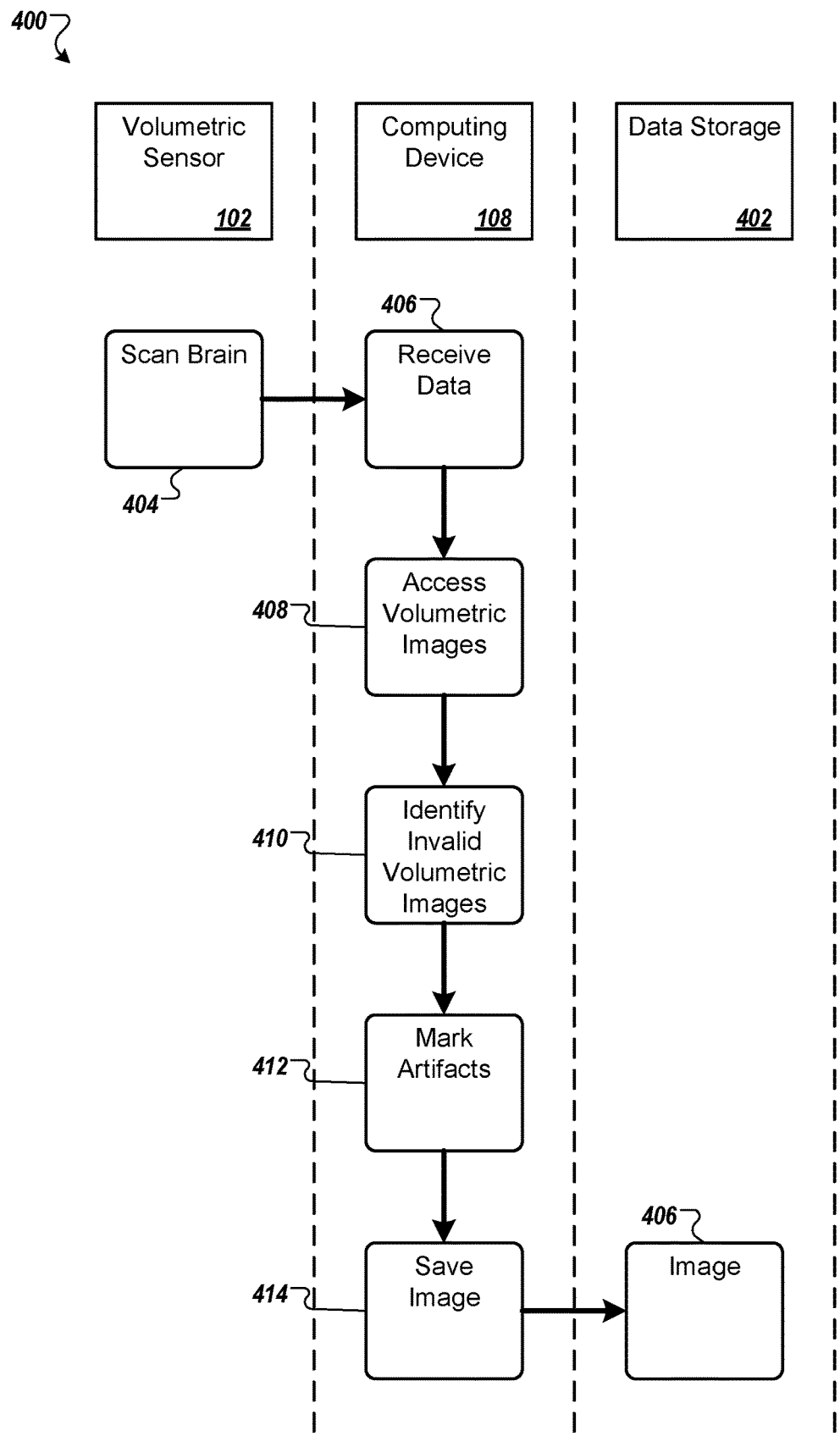
FIGS. 4 and 5 shows flowcharts of example processes for generating a medical image.

FIG. 4 shows a flowchart of an example process 400 for generating a medical image. The process 400 may be used, for example, by the client 108 in preparing the image 110, though it may be used by other systems for other purposes.

The volumetric sensor 102 scans a brain 404. For example, an MRI machine may record a series of sequential brain scans in order to assist a clinician. These scans may generate data based on using magnetic resonance imaging or other medical imaging technique.

The device 108 receives the data 406. For example, a desktop computer may receive scan data generated by the sensing of a subject brain from the MRI machine via an Ethernet data network, and data generated by the MM machine may be transmitted directly to the desktop computer or may be stored in a datastore (e.g., a datastore 402) for access by the desktop computer.

The device 108 accesses volumetric image 408. For example, the desktop computer can parse the data into a sequence of volumetric-images based on the scan data. The desktop can load into memory, for each volumetric image, an associated time. The time may represent a single timestamp for each volumetric image, or a time window in which the data of the volumetric image was collected. The desktop can load into memory, for each volumetric image, data representing a plurality of voxels, each voxel having a particular address in the volumetric image. These voxels may represent a feature of the brain at the time of the scan.

The device 108 can mark some of the volumetric images as containing invalid data 410. For example, the desktop can compare each volumetric image to one or more other volumetric image to identify statistical outliers. One example process for such an examination is described later in the process 500.

In doing so, the desktop can mark at least one, but not all, of the volumetric images as containing invalid data as a result of the process 500. This tagging can be understood as identifying volumetric images that are so unlike other volumetric images that it is likely that the patient moved during the scan. In some cases, such as where a patient is sufficiently still, no such marking may be made.

The device 108 saves an image 414. For example, the desktop computer can compile the volumetric images not marked as invalid into a new image. In some cases, this image may be stored as a four dimensional (4D) image, with the four dimensions being X, Y, and Z in space, and T in time, with one volumetric image at each time point T.

The data storage 402 stores the image. The data storage 402 may be local to the desktop (e.g., installed inside the case as a hard disk) or network-attached (e.g., a remote server that is in data communication with the desktop).

With the image stored in the data storage 402, the desktop or another computer system or device can access the saved image as a motion-corrected image that corrects for invalid data created by operation of a magnetic resonance imaging system. For example, a desktop running computer software can be configured to provide data visualization for: surgical planning, brain network visualization, anomaly detection in brain activity, and segregation of brain networks.

In some cases, the image may be subjected to one or more tests to determine if the image is valid for a particular purpose or general use. For example, in some cases, validating the scan data can include a determination that no more than a discard-threshold number of volumetric-images are tagged as containing invalid data. For example, a discard-threshold number of 1, 2, may be used, or a percentage of 5% may be used, and any image for which more than 1, 2, or 5% of volumetric images were removed may be considered invalid.

Some validation processes may use human input to record expert opinion about validity. For example, an image may be displayed of the image free of the volumetric-images marked as containing invalid data. The user (e.g., a clinician with experience in medical imaging) may provide an input indicating if the image is valid or invalid. The computer can receive, in response to the displaying, user input indicating that the image free of the volumetric-images marked as containing invalid data is usable for a clinical application.

Figure 5:
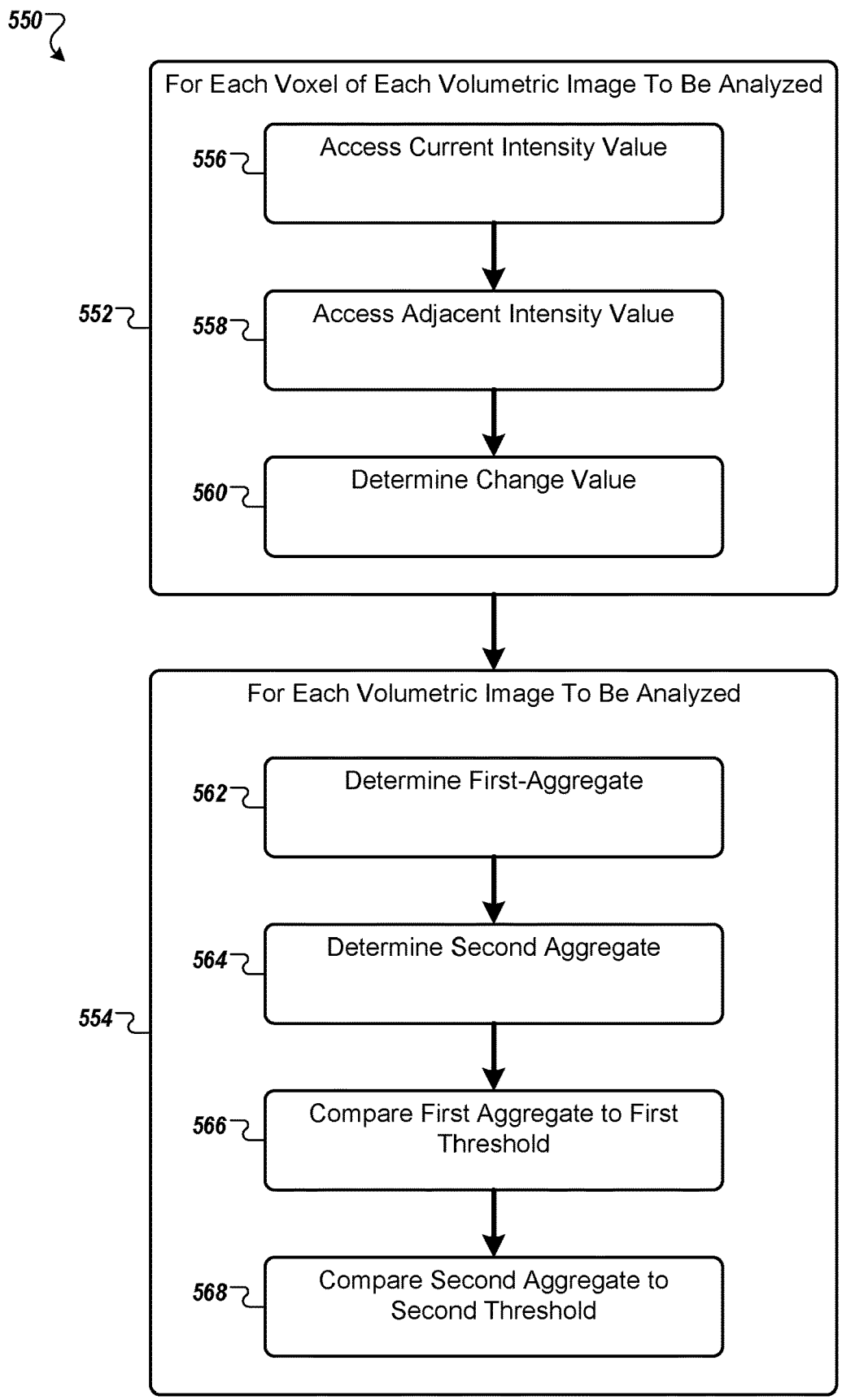

FIG. 5 shows a flowchart of an example process 500 for generating a medical image. The process 500 can be used, for example, to identify invalid volumetric image data 410, though it will be understood that other processes may be used to identify invalid volumetric image data.

In the process 500, each analysis is performed for voxels of each volumetric image to be analyzed 550. As will be described below, voxel values can be compared to voxel values in adjacent volumetric images (e.g., images immediately previous or after in a time-series). In some cases, some available volumetric images may be excluded. For example, the first or last volumetric image may be not be subjected to this analysis as they do not have a previous or following image.

Then, once each voxel to be analyzed has been analyzed, the analysis of the voxels can be aggregated in a per-volumetric-image basis, and the aggregates can be examined to identify outliers. The identification of such an outlier can be used as an analytical indicator that the given volumetric image should be tagged as containing invalid data.

For at least some of the voxels in at least some of the volumetric images, a current intensity value is accessed 556 and an adjacent-intensity value is accessed 558 for comparison. For example, a computer may access each voxel location in a volumetric image, iterating over the entire address space. For a volumetric image having [X,Y,Z] address space, accessing may begin at [0,0,0] and increase one value of the address at a time by one increment until each voxel address is used.

For at least some of the voxels in at least some of the volumetric images, a change value for the voxel is found 560 by comparing the current-intensity value of the voxel to the adjacent-intensity value of the comparison voxel. For example, the computer may look up the voxel value at the same address in an adjacent volumetric-image. That is to say, a voxel value of the current image at [3, 25, 174] (e.g. a value of 0.753) can be compared to an adjacent image's voxel value at [3, 25, 174] (e.g., a value of 0.755) and a comparison can be made (e.g., an absolute value of a subtraction resulting in |0.753−0.755|=0.002).

For at least some of the plurality volumetric images, a first-aggregate is found 562 using at least a mean value of all change values of the volumetric image. For example, for a given volumetric image, a computer may find the summation of each change value, and then the summation can be divided by the total number of voxels in the volumetric image, though other mean calculations can be used.

In some cases, the mean value can be increased with a first function that grows at a first rate greater than linearly. For example, the mean value may be subjected to a squaring function where the mean value is squared. In another example, the mean value may be subjected to a function that returns a value of zero if the mean is lower than a given threshold, which may be used to conceptually "throw out" small values. In some examples, the given threshold may be a statistical function (e.g., one standard deviation, half of a standard deviation, two standard deviations) of the mean across all volumetric images. However, other given thresholds can be used, such as a constant, predetermined value.

For at least some of the plurality of volumetric images, a second-aggregate is found 564 using at least a median value of all change values of the volumetric image. For example, for a given volumetric image, a computer may arrange all change values in order of value and may identify a central value, though other median calculations can be used.

In some cases, the median value can be increased with a second function that grows at a second rate greater than linearly. For example, the median value may be subjected to a squaring function where the mean value is squared. In another example, the median value may be subjected to a function that returns a value of zero if the median is lower than a given threshold, which may be used to conceptually "throw out" small values. In some examples, the given threshold may be a statistical function (e.g., one standard deviation, half of a standard deviation, two standard deviations) of the mean across all volumetric images. However, other given thresholds can be used, such as a constant, predetermined value.

The first rate may be the same or different from the second rate. For example, the mean value and the median value may both be subjected to the same function (e.g., squaring the value), in order to scale them both at the same rate. In another example, the median may be subjected to a first function (e.g., squaring) while the mean may be subjected to a different function (e.g., cubing). In some cases, using functions with different points of inflection can change the profile at which abnormality is penalized. As such, this can be adjusted fine-tune the process between detecting significant micro abnormalities at a voxel level to overall macro abnormalities at a volumetric image level, which may be beneficial for a given imaging machine, patient type, or process being used.

For at least some of the plurality volumetric images, the first-aggregate is compared 566 to a first threshold and a second-aggregate is compared 568 to a second threshold. For example, the thresholds can be determined using the same or different processes. The first threshold may be determined at a given number (e.g., 0.5 1, 2, 2.5) of standard deviations from the mean of all test data while the second threshold is calculated based on a linear scaling factor (e.g., 0.5, 1, 2, 2.5) of the median.

In general, the use of the mean in 562 can be used to identify small movements by a patient, while the use of a median in 564 can be used to identify large movements by a patient. As will be understood, patients often physically have a significant degree of freedom of movement when being imaged. Even when instructed to remain still, the patient may voluntarily or involuntarily move during imaging. This process can identify both large and small motions, where use of mean alone may miss large movements and the use of median alone may miss small movements. As such, this technology can advantageously improve health outcomes by producing useful images in less time. This advantage is particularly important, improving healthcare and even saving lives, when treatment is time-sensitive or when a patient is seeking care for a condition that causes them to engage in movement.

Other processes similar to the process 500 may be used for the same or similar purposes. For example, instead of using an adjacent-intensity value for finding the change value 560, a different baseline may be used. This can include generating a baseline by combining multiple voxel values (e.g., from the first and last volumetric image, from randomly selected volumetric images, from every Nth volumetric image) or by using voxel values from a single reference volumetric image (e.g., the first or last volumetric image).

Figure 6:
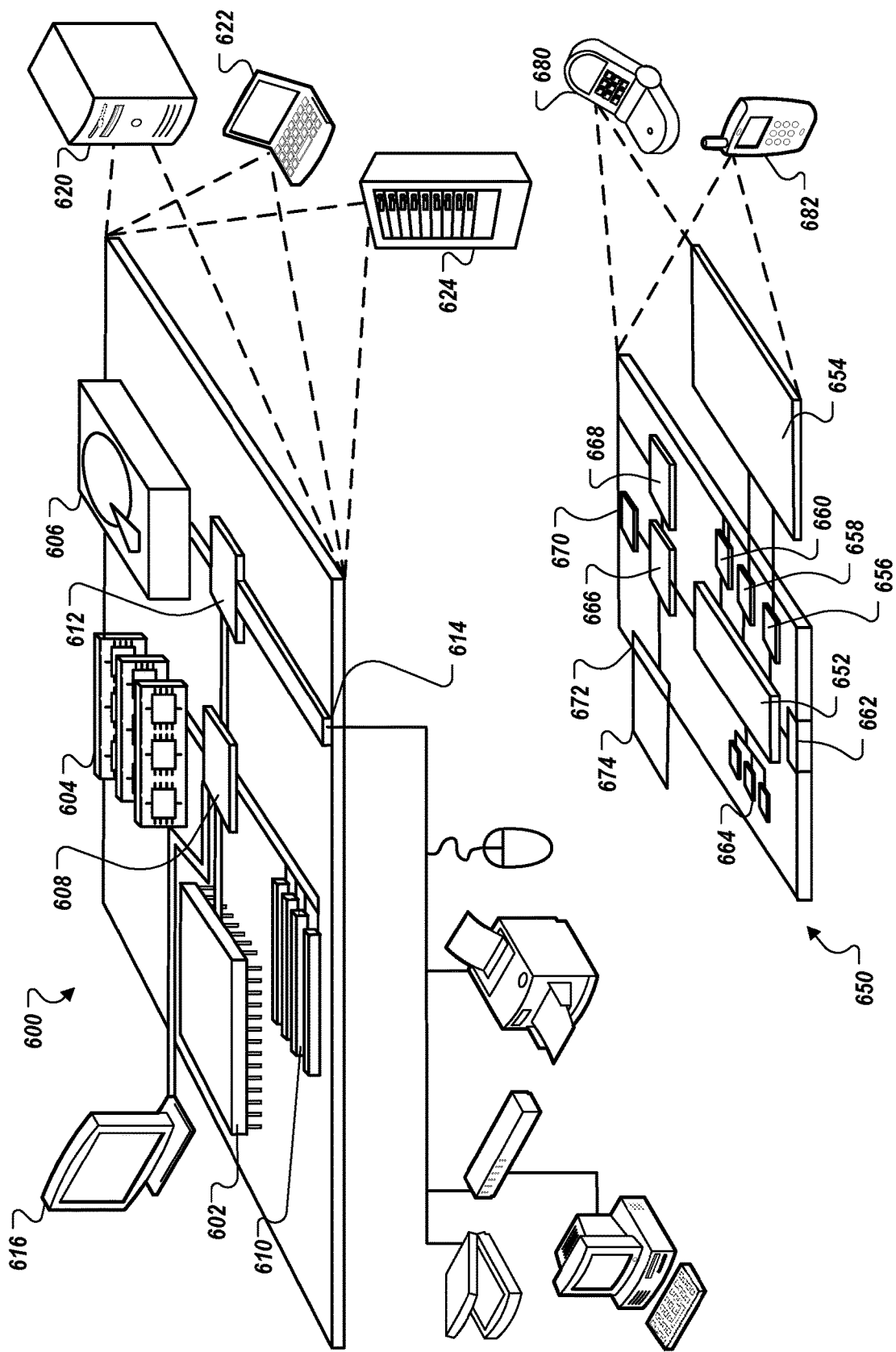
FIG. 6 is a schematic diagram that shows an example of a computing device and a mobile computing device.

FIG. 6 shows an example of a computing device 600 and an example of a mobile computing device that can be used to implement the techniques described here. The computing device 600 is intended to represent various forms of digital computers, such as laptops, desktops, workstations, personal digital assistants, servers, blade servers, mainframes, and other appropriate computers. The mobile computing device is intended to represent various forms of mobile devices, such as personal digital assistants, cellular telephones, smart-phones, and other similar computing devices. The components shown here, their connections and relationships, and their functions, are meant to be exemplary only, and are not meant to limit implementations of the inventions described and/or claimed in this document.

The computing device 600 includes a processor 602, a memory 604, a storage device 606, a high-speed interface 608 connecting to the memory 604 and multiple high-speed expansion ports 610, and a low-speed interface 612 connecting to a low-speed expansion port 614 and the storage device 606. Each of the processor 602, the memory 604, the storage device 606, the high-speed interface 608, the high-speed expansion ports 610, and the low-speed interface 612, are interconnected using various busses, and can be mounted on a common motherboard or in other manners as appropriate. The processor 602 can process instructions for execution within the computing device 600, including instructions stored in the memory 604 or on the storage device 606 to display graphical information for a GUI on an external input/output device, such as a display 616 coupled to the high-speed interface 608. In other implementations, multiple processors and/or multiple buses can be used, as appropriate, along with multiple memories and types of memory. Also, multiple computing devices can be connected, with each device providing portions of the necessary operations (e.g., as a server bank, a group of blade servers, or a multi-processor system).

The memory 604 stores information within the computing device 600. In some implementations, the memory 604 is a volatile memory unit or units. In some implementations, the memory 604 is a non-volatile memory unit or units. The memory 604 can also be another form of computer-readable medium, such as a magnetic or optical disk.

The storage device 606 is capable of providing mass storage for the computing device 600. In some implementations, the storage device 606 can be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product can also contain instructions that, when executed, perform one or more methods, such as those described above. The computer program product can also be tangibly embodied in a computer- or machine-readable medium, such as the memory 604, the storage device 606, or memory on the processor 602.

The high-speed interface 608 manages bandwidth-intensive operations for the computing device 600, while the low-speed interface 612 manages lower bandwidth-intensive operations. Such allocation of functions is exemplary only. In some implementations, the high-speed interface 608 is coupled to the memory 604, the display 616 (e.g., through a graphics processor or accelerator), and to the high-speed expansion ports 610, which can accept various expansion cards (not shown). In the implementation, the low-speed interface 612 is coupled to the storage device 606 and the low-speed expansion port 614. The low-speed expansion port 614, which can include various communication ports (e.g., USB, Bluetooth, Ethernet, wireless Ethernet) can be coupled to one or more input/output devices, such as a keyboard, a pointing device, a scanner, or a networking device such as a switch or router, e.g., through a network adapter.

The computing device 600 can be implemented in a number of different forms, as shown in the figure. For example, it can be implemented as a standard server 620, or multiple times in a group of such servers. In addition, it can be implemented in a personal computer such as a laptop computer 622. It can also be implemented as part of a rack server system 624. Alternatively, components from the computing device 600 can be combined with other components in a mobile device (not shown), such as a mobile computing device 650. Each of such devices can contain one or more of the computing device 600 and the mobile computing device 650, and an entire system can be made up of multiple computing devices communicating with each other.

The mobile computing device 650 includes a processor 652, a memory 664, an input/output device such as a display 654, a communication interface 666, and a transceiver 668, among other components. The mobile computing device 650 can also be provided with a storage device, such as a micro-drive or other device, to provide additional storage. Each of the processor 652, the memory 664, the display 654, the communication interface 666, and the transceiver 668, are interconnected using various buses, and several of the components can be mounted on a common motherboard or in other manners as appropriate.

The processor 652 can execute instructions within the mobile computing device 650, including instructions stored in the memory 664. The processor 652 can be implemented as a chipset of chips that include separate and multiple analog and digital processors. The processor 652 can provide, for example, for coordination of the other components of the mobile computing device 650, such as control of user interfaces, applications run by the mobile computing device 650, and wireless communication by the mobile computing device 650.

The processor 652 can communicate with a user through a control interface 658 and a display interface 656 coupled to the display 654. The display 654 can be, for example, a TFT (Thin-Film-Transistor Liquid Crystal Display) display or an OLED (Organic Light Emitting Diode) display, or other appropriate display technology. The display interface 656 can comprise appropriate circuitry for driving the display 654 to present graphical and other information to a user. The control interface 658 can receive commands from a user and convert them for submission to the processor 652. In addition, an external interface 662 can provide communication with the processor 652, so as to enable near area communication of the mobile computing device 650 with other devices. The external interface 662 can provide, for example, for wired communication in some implementations, or for wireless communication in other implementations, and multiple interfaces can also be used.

The memory 664 stores information within the mobile computing device 650. The memory 664 can be implemented as one or more of a computer-readable medium or media, a volatile memory unit or units, or a non-volatile memory unit or units. An expansion memory 674 can also be provided and connected to the mobile computing device 650 through an expansion interface 672, which can include, for example, a SIMM (Single In Line Memory Module) card interface. The expansion memory 674 can provide extra storage space for the mobile computing device 650, or can also store applications or other information for the mobile computing device 650. Specifically, the expansion memory 674 can include instructions to carry out or supplement the processes described above, and can include secure information also. Thus, for example, the expansion memory 674 can be provide as a security module for the mobile computing device 650, and can be programmed with instructions that permit secure use of the mobile computing device 650. In addition, secure applications can be provided via the SIMM cards, along with additional information, such as placing identifying information on the SIMM card in a non-hackable manner.

The memory can include, for example, flash memory and/or NVRAM memory (non-volatile random access memory), as discussed below. In some implementations, a computer program product is tangibly embodied in an information carrier. The computer program product contains instructions that, when executed, perform one or more methods, such as those described above. The computer program product can be a computer- or machine-readable medium, such as the memory 664, the expansion memory 674, or memory on the processor 652. In some implementations, the computer program product can be received in a propagated signal, for example, over the transceiver 668 or the external interface 662.

The mobile computing device 650 can communicate wirelessly through the communication interface 666, which can include digital signal processing circuitry where necessary. The communication interface 666 can provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication can occur, for example, through the transceiver 668 using a radio-frequency. In addition, short-range communication can occur, such as using a Bluetooth, WiFi, or other such transceiver (not shown). In addition, a GPS (Global Positioning System) receiver module 670 can provide additional navigation- and location-related wireless data to the mobile computing device 650, which can be used as appropriate by applications running on the mobile computing device 650.

The mobile computing device 650 can also communicate audibly using an audio codec 660, which can receive spoken information from a user and convert it to usable digital information. The audio codec 660 can likewise generate audible sound for a user, such as through a speaker, e.g., in a handset of the mobile computing device 650. Such sound can include sound from voice telephone calls, can include recorded sound (e.g., voice messages, music files, etc.) and can also include sound generated by applications operating on the mobile computing device 650.

The mobile computing device 650 can be implemented in a number of different forms, as shown in the figure. For example, it can be implemented as a cellular telephone 680. It can also be implemented as part of a smart-phone 682, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

While this document describes this technology in terms of medical imaging, it will be appreciated that other types of volumetric imaging may benefit from this technology. For example, some manufacturing processes can be tested with volumetric imaging that may be subject to movement-based invalid data, and may be improved with the incorporation of this technology.

What is claimed is:

1. A method of generating an image, the method comprising:
   receiving scan data generated by sensing of a subject brain as the subject brain is moved by involuntary movement of the subject;
   accessing a sequence of volumetric-images based on the scan data, each volumetric image having an associated time and comprising a plurality of voxels, each voxel having a particular address in the volumetric image;
   for at least some of the voxels in at least some of the volumetric images:
   accessing a current-intensity value for the voxel;
      accessing an adjacent-intensity value for a comparison voxel with the particular address in an adjacent volumetric-image that is temporally adjacent in the sequence of volumetric images; and
      determining a change value for the voxel by comparing the current-intensity value of the voxel to the adjacent-intensity value of the comparison voxel; for at least some of the volumetric images;
      determine a first-aggregate using at least a mean value of all change values of the volumetric image;
      determine a second-aggregate using at least a median value of all change values of the volumetric image;
      comparing the first-aggregate to a first threshold;
      comparing a second-aggregate to a second threshold;
   identifying movement based on the mean and the median values or the comparison;
   marking at least one, but not all, of the volumetric images as invalid as a result of the comparison of the first-aggregate to the first threshold and the comparison of the second-aggregate to the second threshold;
   saving in computer memory an image without the volumetric images that have been marked as invalid; and
   accessing the saved image as a motion-corrected image that corrects for artifacts created by operation of a magnetic resonance imager that do not correctly represent a phenomenon of the subject brain.

2. The method of claim 1, wherein
determining a first-aggregate comprises:
   determining a mean value of all change values of the volumetric image;
   increasing the mean value with a first function that grows at a first rate greater than linearly; and
determining a second-aggregate comprises:
   determining a median value of all change values of the volumetric image; and
   increasing the mean value with a second function that grows at a second rate greater than linearly.

3. The method of claim 2, wherein the first rate is equivalent to the second rate.

4. The method of claim 1, the method further comprising:
validating the scan data based on a determination that no more than a discard-threshold number of volumetric-images have been marked as invalid.

5. The method of claim 1, the method further comprising validating the first threshold and validating the second threshold based in part on:
   displaying the image without the volumetric-images that have been marked as invalid; and
   receiving, in response to the displaying, user input indicating that the image without the volumetric-images that have been marked as invalid is usable for a clinical application.

6. The method of claim 1, the method further comprising, for at least some of the voxels in at least some of the volumetric images, accessing the particular address of the voxel.

7. A non-transitory computer-readable media for tangibly storing instructions for generation of an image, the computer-readable media storing instructions that, when executed by one or more processors, cause the one or more processors to perform operations comprising:
   receiving scan data generated by sensing of a subject brain as the subject brain is moved by involuntary movement of the subject;
   accessing a sequence of volumetric-images based on the scan data, each volumetric image having an associated time and comprising a plurality of voxels, each voxel having a particular address in the volumetric image;
   for at least some of the voxels in at least some of the volumetric images: accessing a current-intensity value for the voxel;
      accessing an adjacent-intensity value for a comparison voxel with the particular address in an adjacent volumetric-image that is temporally adjacent in the sequence of volumetric images; and
      determining a change value for the voxel by comparing the current-intensity value of the voxel to the adjacent-intensity value of the comparison voxel; for at least some of the volumetric images;
      determine a first-aggregate using at least a mean value of all change values of the volumetric image;
      determine a second-aggregate using at least a median value of all change values of the volumetric image;
      comparing the first-aggregate to a first threshold;
      comparing a second-aggregate to a second threshold;
   identifying movement based on the mean and the median values or the comparison;
   marking at least one, but not all, of the volumetric images as invalid as a result of the comparison of the first-aggregate to the first threshold and the comparison of the second-aggregate to the second threshold;
   saving in computer memory an image without the volumetric images that have been marked as invalid; and
   accessing the saved image as a motion-corrected image that corrects for artifacts created by operation of a magnetic resonance imager that do not correctly represent a phenomenon of the subject brain.

8. The media of claim 7, wherein
determining a first-aggregate comprises:
   determining a mean value of all change values of the volumetric image;
   increasing the mean value with a first function that grows at a first rate greater than linearly; and
determining a second-aggregate comprises:
   determining a median value of all change values of the volumetric image; and
   increasing the mean value with a second function that grows at a second rate greater than linearly.

9. The media of claim 8, wherein the first rate is equivalent to the second rate.

10. The media of claim 7, the operations further comprising:
  validating the scan data based on a determination that no more than a discard-threshold number of volumetric-images have been marked as invalid.

11. The media of claim 7, the operations further comprising validating the first threshold and validating the second threshold based in part on:
  displaying the image without the volumetric-images that have been marked as invalid; and
  receiving, in response to the displaying, user input indicating that the image without the volumetric-images that have been marked as invalid is usable for a clinical application.

12. The media of claim 7, the operations further comprising, for at least some of the voxels in at least some of the volumetric images, accessing the particular address of the voxel.

13. A system for generating volumetric images, the system comprising:
  a volumetric sensor; and
  an element comprising one or more processors and computer memory:
    adapted to receive scan data generated by sensing of a subject brain as the subject brain is moved by involuntary movement of the subject; and
    configured to perform operations comprising:
      accessing a sequence of volumetric-images based on the scan data, each volumetric image having an associated time and comprising a plurality of voxels, each voxel having a particular address in the volumetric image;
      for at least some of the voxels in at least some of the volumetric images:
        accessing a current-intensity value for the voxel;
        accessing an adjacent-intensity value for a comparison voxel with the particular address in an adjacent volumetric-image that is temporally adjacent in the sequence of volumetric images; and
        determining a change value for the voxel by comparing the current-intensity value of the voxel to the adjacent-intensity value of the comparison voxel;
      for at least some of the volumetric images:
        determine a first-aggregate using at least a mean value of all change values of the volumetric image;
        determine a second-aggregate using at least a median value of all change values of the volumetric image;
        comparing the first-aggregate to a first threshold;
        comparing a second-aggregate to a second threshold;
        identifying movement based on the mean and the median values or the comparison;
        marking at least one, but not all, of the volumetric images as invalid as a result of the comparison of the first-aggregate to the first threshold and the comparison of the second-aggregate to the second threshold;
      saving in computer memory an image without the volumetric images that have been marked as invalid; and
    accessing the saved image as a motion-corrected image that corrects for artifacts created by operation of a magnetic resonance imager that do not correctly represent a phenomenon of the subject brain.

14. The system of claim 13, wherein
determining a first-aggregate comprises:
  determining a mean value of all change values of the volumetric image;
  increasing the mean value with a first function that grows at a first rate greater than linearly; and
determining a second-aggregate comprises:
  determining a median value of all change values of the volumetric image; and
  increasing the mean value with a second function that grows at a second rate greater than linearly.

15. The system of claim 14, wherein the first rate is equivalent to the second rate.

16. The system of claim 13, the operations further comprising:
  validating the scan data based on a determination that no more than a discard-threshold number of volumetric-images that have been marked as invalid.

17. The system of claim 13, the operations further comprising validating the first threshold and validating the second threshold based in part on:
  displaying the image without the volumetric-images that have been marked as invalid; and
  receiving, in response to the displaying, user input indicating that the image without the volumetric-images that have been marked as invalid is usable for a clinical application.

18. The system of claim 13, the operations further comprising, for at least some of the voxels in at least some of the volumetric images, accessing the particular address of the voxel.

* * * * *